United States Patent [19]

Hammerschmidt et al.

[11] Patent Number: 4,795,596

[45] Date of Patent: Jan. 3, 1989

[54] 1-AMINOMETHYLNAPHTHALENE-6-SULPHONIC ACID, ITS PREPARATION AND ITS USE

[75] Inventors: Erich Hammerschmidt, Bergisch; Heinz U. Blank, Odenthal, both of Fed. Rep. of Germany

[73] Assignee: Bayer Aktiengesellschaft, Leverkusen, Fed. Rep. of Germany

[21] Appl. No.: 108,525

[22] Filed: Oct. 15, 1987

[30] Foreign Application Priority Data

Oct. 31, 1986 [DE] Fed. Rep. of Germany ....... 3637138

[51] Int. Cl.$^4$ ............................................. C07C 143/60
[52] U.S. Cl. ...................................... 260/508; 562/467
[58] Field of Search ........................................... 260/508

[56] References Cited

U.S. PATENT DOCUMENTS 1,785,955 12/1930 Herzberg et al. ................... 260/508

Primary Examiner—Nicky Chan
Attorney, Agent, or Firm—Sprung, Horn Kramer & Woods

[57] ABSTRACT

The invention relates to the new compound 1-aminomethylnaphthalene-6-sulphonic acid, a process for its preparation by amidoalkylation of naphthalene-2-sulphonic acid and hydrolysis of the amidoalkylation product, and its use as an intermediate product for the preparation of 6-hydroxynaphthalene-1-carboxylic acid.

1 Claim, No Drawings

1-AMINOMETHYLNAPHTHALENE-6-SULPHONIC ACID, ITS PREPARATION AND ITS USE

The invention relates to the new compound 1-aminomethylnaphthalene-6-sulphonic acid, a process for its preparation and its use as an intermediate product for the preparation of 6-hydroxynaphthalene-1-carboxylic acid.

6-Hydroxynaphthalene-1-carboxylic acid is an important intermediate product for the preparation of biologically active compounds, for example the drug tolrestat (see, for example, European Patent No. A1-0,059,596). 6-Hydroxynaphthalene-1-carboxylic acid is also used as a component for the preparation of polyesters (see, for example, Japanese Patent No. 134,778).

In view of the importance of 6-hydroxynaphthalene-1-carboxylic acid, there is therefore great industrial interest in an economical process for the preparation of this compound on an industrial scale.

Various synthesis routes are already known for the preparation of 6-hydroxynaphthalene-1-carboxylic acid; however, these all have serious disadvantages, and in particular they start from expensive starting compounds, some of which are not even accessible in industrial amounts, and/or require reactions which for reasons of industrial hygiene and environmental technology can be carried out only with high expenditure on apparatus, if at all, and/or lead to poor yields.

These known synthesis routes are, in detail, the following processes:

Process 1

The starting substance here is 1-aminonaphthalene-6-sulphonic acid (1,6-Cleve's acid); this is diazotized and converted into 1-cyanonaphthalene-6-sulphonic acid by a Sandmeyer reaction with alkali metal cyanides in the presence of heavy metals (for example copper). This product is converted into 6-hydroxynaphthalene-1-carboxylic acid by hydrolysis and subsequent fusion with an alkali (see Ullmanns Enzyklopädie der technischen Chemie (Ullmann's Encyclopaedia of Industrial Chemistry), 4th edition, volume 17, page 89 and the detailed description of this synthesis route in Soc. 1923, pages 1641–1645).

The disadvantages of this process are that the pure, that is to say isomer-free, 1,6-Cleve's acid required for the reaction is a relatively expensive starting compound, and that the Sandmeyer reaction, because of the use of alkali metal cyanides and heavy metals, requires a high expenditure on apparatus and process and safety technology.

Process 2

This also starts from pure 1,6-Cleve's acid; this is acylated, however. The 1-acylaminonaphthalene-6-sulphonic acid obtained in this manner is then converted into 1-iodo-6-methoxy-naphthalene in a reaction which proceeds via several stages, and this product is converted into 6-methoxynaphthalene-1-carboxylic acid in a Grignard reaction with magnesium and carbon dioxide (see B. 68, page 2087 et seq. (1936)).

Apart from the fact that this process also starts from the expensive 1,6-Cleve's acid, the process is unsuitable for preparation of 6-hydroxy-naphthalene-1-carboxylic acid on an industrial scale because it is cumbersome and the individual reaction stages (for example the Grignard reaction) are difficult to carry out.

Process 3

This starts from naphthalene-1-carboxylic acid; this is sulphonated, and the pure 1-carboxy-naphthalene-6-sulphonic acid isolated from the isomer mixture obtained from the sulphonation is converted into 6-hydroxynaphthalene-1-carboxylic acid by alkali fusion (see Soc. 1923, pages 1641–1647, in particular 1645–1646).

The disadvantages of this process are that naphthalene-1-carboxylic acid is expensive and can be obtained on an industrial scale only with difficulty, and furthermore that the yield of 1-carboxynaphthalene-6-sulphonic acid in the sulphonation mixture obtained from the sulphonation is low and isolation of the 1-carboxynaphthalene-6-sulphonic acid from this mixture is associated with considerable difficulties and further losses in yield.

Process 4

This starts from 6-alkoxytetralone; this is converted into 6-alkoxy-naphthalene-1-carboxylic acid via 6-alkoxy-1-cyano-3,4-dihydronaphthalene and 6-alkoxy-1-cyano-naphthalene (see U.S. Pat. No. 4,590,010; and J. Org. Chem. 1983, pages 5134–5135).

The disadvantages of this process are that this starts from an expensive speciality chemical, 6-methoxytetralone, and that cyanation of this in organic solvents with alkali metal cyanides in the presence of stoichiometric amounts of a Lewis acid using phase transfer catalysts or—according to J. Org. Chem. 1983 loc. cit.—with trimethylsilyl cyanide, boron trifluoride, pyridine and phosphorus oxychloride, cannot be carried out on an industrial scale for reasons of industrial hygiene and environmental technology.

Process 5

This starts from anisole; this is reacted with furan-2-carboxylic acid in the presence of a large excess of aluminium trichloride to give 6-methoxy-naphthalene-1-carboxylic acid (see J. Am. Chem. Soc. 69, page 2262 and European Patent No. A1-200,840).

The process is unsuitable for preparation of 6-hydroxynaphthalene-1-carboxylic acid on an industrial scale because of the expensive starting compounds to be used in it, the large amounts of aluminium chloride required and the poor yields achieved with it at the same time.

It has now been found that 6-hydroxynaphthalene-1-carboxylic acid can be obtained by a synthesis route which can be carried out industrially without difficulties from an inexpensive starting material which is available in industrial amounts, by a procedure in which naphthalene-2-sulphonic acid is used as the starting substance, this is amidomethylated in a manner which is known per se, the amidomethylation products are hydrolysed, the 1-aminomethylnaphthalene-6-sulphonic acid obtained after this hydrolysis is oxidized to 1-carboxynaphthalene-6-sulphonic acid in a manner which is known per se and this is converted into 6-hydroxynaphthalene-1-carboxylic acid by alkali fusion.

Surprisingly, it has been found that hydrolysis of the reaction mixture which is obtained from amidoalkylation of naphthalene-2-sulphonic acid and contains isomers and by-products gives pure, virtually isomer-free 1-aminomethylnaphthalene-6-sulphonic acid directly.

1-Aminomethylnaphthalene-6-sulphonic acid and its preparation are new. The fact that the 1-aminomethylnaphthalene-6-sulphonic acid is obtainable in a pure form from naphthalene-2-sulphonic acid in a simple manner without difficulties and can be converted into the desired 6-hydroxynaphthalene-1-carboxylic acid in a reaction sequence which can also be carried out without difficulties on an industrial scale opens up a new interesting synthesis route for the preparation of 6-hydroxynaphthalene-1-carboxylic acid from naphthalene-2-sulphonic acid.

The invention therefore relates to the new compound 1-aminomethylnaphthalene-6-sulphonic acid

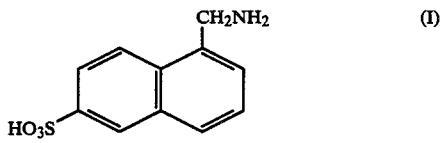

(I)

a process for its preparation and its use for the preparation of 6-hydroxynaphthalene-1-carboxylic acid.

The process according to the invention for the preparation of 1-aminomethylnaphthalene-6-sulphonic acid is characterized in that naphthalene-2-sulphonic acid is amidoalkylated in a manner which is known per se in an acid medium with compounds of the formula

(II)

in which
$R_1$ represents an acyl radical,
$R_2$ represents an acyl radical or, preferably, a hydrogen atom, or $R_1$ and $R_2$ together form a diacyl radical,
X represents a halogen atom, an $R_3O-$ group or an $(R_1)(R_2)N-$ group and
$R_3$ represents an acyl radical or an $(R_1)(R_2)N-CH_2-$ radical or, preferably, a hydrogen atom, and the acyl radical $R_1$ or the acyl radicals $R_1$ and $R_2$ are then split off from the amidoalkylation product by acid or alkaline hydrolysis.

The amidoalkylation, according to the invention, of naphthalene-2-sulphonic acid with the compounds of the formula (II) is carried out in a manner which is known per se for amidoalkylation of aromatic compounds; such amidoalkylations of aromatic compounds are described, for example, in Org. Reactions 14, page 52 et seq.; Synthesis 1970, page 49 et seq. and Synthesis 1984, page 85 et seq., and furthermore in DE-OS (German Published Specification) Nos. 2,264,698 and 3,408,300. Naphthalene-2-sulphonic acid and the amidoalkylating agent are reacted in a molar ratio of about 1:0.6 to 1:1.4 at temperatures from 0° to 100° C., preferably in 60 to 100% strength by weight sulphuric acid.

The naphthalene-2-sulphonic acid can be used in the form of the free acid or in the form of its salts. It can be used in the pure form or as a mixture with other naphthalene-mono- and di-sulphonic acids.

Naphthalene-2-sulphonic acid is preferably used as the sodium salt or in the form of sulphonation mixtures, such as are obtained in the reaction of 1 mole of naphthalene with 0.8 to 2.0 mole of 98-100% strength sulphuric acid at temperatures of 100° to 170° C. The content of naphthalene-2-sulphonic acid in these sulphonation mixtures is in general 40 to 70% by weight.

Possible amidoalkylating agents of the formula (II) are the most diverse amidoalkylating agents. Acyl radicals which may be mentioned for $R_1$ and $R_2$ are the radicals of aliphatic and aromatic carboxylic and sulphonic acids, and acyl radicals which may be mentioned for $R_3$ are the radicals of aliphatic and aromatic carboxylic acids. Examples which may be mentioned of acyl radicals of aliphatic carboxylic acids are: $C_1-C_4$-alkanoyl or $C_1-C_4$-alkenoyl radicals which are optionally substituted by chlorine atoms, such as the formyl, acetyl, propionyl, chloroacetyl or acryloyl radical; examples which may be mentioned of radicals of aromatic carboxylic acids are the benzoyl, isophthaloyl or terephthaloyl radical. An example which may be mentioned of radicals of aliphatic sulphonic acids is the methanesulphonyl radical, and examples which may be mentioned of radicals of aromatic sulphonic acids are the benzenesulphonyl and the p-toluenesulphonyl radical. $R_1$ and $R_2$ can furthermore together form a diacyl radical of a saturated or unsaturated aliphatic dicarboxylic acid or of an aromatic o-dicarboxylic acid. Examples which may be mentioned of radicals of such dicarboxylic acids are the radicals of adipic, maleic and phthalic acid.

Preferred compounds of the formula (II) are those in which
$R_1$ represents a $C_1-C_4$-alkanoyl or $C_1-C_4$-alkenoyl radical which is optionally substituted by chlorine, or the radical of an aromatic carboxylic acid and $R_2$ represents hydrogen, or
$R_1$ and $R_2$ together form the diacyl radical of a saturated or unsaturated aliphatic dicarboxylic acid or of an aromatic o-dicarboxylic acid and
X represents chlorine or a hydroxyl or $R_1NH$ group.

Particularly preferred amidoalkylating agents of the formula (II) are N-hydroxymethylacetamide, N-hydroxymethylchloroacetamide, N-hydroxymethylbenzamide, N-hydroxymethylphthalimide, N,N'-(bishydroxymethyl)-isophthalic acid diamide and -terephthalic acid diamide and bis-benzamidomethane.

The hydroxymethyl group containing amidoalkylating agents can be used in the form of the pure compounds but also in the form of the reaction products as are obtained in the reaction of the corresponding amides with stoichiometric amounts of formaldehyde or paraformaldehyde. If the amides are reacted with aqueous formaldehyde solutions solutions or suspensions of the reaction products in water are obtained; if the reaction is carried out with paraformaldehyde solid or liquid reaction products are obtained. These liquid or solid reaction products or their aqueous solutions and suspensions can be used directly in the amidoalkylation reaction.

The hydrolysis of the 1-N-acylamido- or 1-N-acylimido-methylnaphthalene-6-sulphonic acids to give 1-aminomethyl-naphthalene-6-sulphonic acid is carried out in a manner which is known per se for splitting off acyl groups from amido groups (see DE-OS (German Published Specification) Nos. 2,264,698 and 3,408,300, and Houben-Weyl volume 11/1, pages 927–931).

When the hydrolysis has ended, the pH value of the alkaline hydrolysis mixture is brought to a value $\leq 6.5$, preferably $\leq 6$, by addition of acid. The free 1-aminomethylnaphthalene-6-sulphonic acid which separates out as a precipitate is then separated off mechanically, for example by filtration or filtration with suction or centrifugation. In the case of acid hydrolysis, the free 1-aminomethylnaphthalene-6-sulphonic acid precipitates out of the reaction mixture immediately after being formed and is isolated from this.

The 1-aminomethylnaphthalene-6-sulphonic acid can be converted into 1-formylnaphthalene-6-sulphonic acid in a manner which is known per se by a Sommelet reaction (see, for example, Houben Weyl, Methoden der Organischen Chemie (Methods of Organic Chemistry), 4th edition, volume 7/1 page 198 or Organic Reactions 8, 197 (1954)), that is to say by reaction with hexamethylenetetramine. The 1-formylnaphthalene-6-sulphonic acid is in turn oxidized by processes known for the oxidation of aldehydes to carboxylic acids (see, for example, Houben Weyl loc. cit. volume 8, pages 407–413), for example by oxidation with permanganate (see, for example, Houben Weyl, volume 4 I/b, pages 615–621), to give 1-carboxynaphthalene-6-sulphonic acid.

In another process, the 1-aminomethylnaphthalene-6-sulphonic acid is oxidized directly in a manner which is known per se by means of dichromate salts or chromate salts in a neutral to alkaline medium to give 1-carboxynaphthalene-6-sulphonic acid (see, for example, Houben-Weyl, volume 4/1B, page 435).

EXAMPLE 1

1,032 g of 95% strength by weight sulphuric acid are taken and 230 g (1 mol) of naphthalene-2-sulphonic acid (sodium salt) and 151 g (1 mol) of N-hydroxymethylbenzamide are simultaneously introduced at 15° to 20° C. in the course of one hour, with stirring. The reaction mixture is stirred at 20° to 25° C. for 3 hours and then stirred into 4,160 g of 25% strength sodium hydroxide solution. The resulting hot alkaline suspension is warmed at 140° C. in an autoclave for 4 hours to hydrolyse the benzamidomethyl compound. The hot alkaline reaction solution is then acidified to a pH value of 6.0; after cooling to 35° C., the 1-aminomethylnaphthalene-6-sulphonic acid, sparingly soluble as the inner salt, is filtered off and washed with water.

After drying, 149.5 g (=60% of theory) of 1-aminomethylnaphthalene-6-sulphonic acid is obtained in the form of ivory-coloured crystals. Degree of purity of the acid: 95.2%. The product also contains 0.3% by weight of isomers, 0.6% by weight of water and 3.9% by weight of sodium sulphate.

NMR spectrum of 1-aminomethylnaphthalene-6-sulphonic acid (NaOD): δ3.75 (s, 2H), 7.10 (d, 1H), 7.19 (m, 1H), 7.49 (d, 1H), 7.63–7.67 (s, 2H), 8.08 (s, 1H).

Empirical formula $C_{11}H_{11}NO_3S$

Elemental analysis (of the 100% pure compound): calculated: C 55.68%, H 4.67%, N 5.90%; found: C 55.60%, H 4.72%, N 5.94%.

EXAMPLE 2

300.4 g of sulphonation mixture which has been obtained from sulphonation of naphthalene with sulphuric acid (100% strength) and had the following composition (% data=% by weight).

0.51% of naphthalene-2,6-di-sulphonic acid,
0.25% of naphthalene-1,5-disulphonic acid,
1.47% of naphthalene-2,7-disulphonic acid,
3.77% of naph-thalene-1,6-disulphonic acid,
2.52% naphthalene-1,7-disulphonic acid,
0.52% of naphthalene-1,3-disulphonic acid
3.37% of naphthalene-1-sulphonic acid,
65.86% of naphthalene-2-sulphonic acid,
0.20% of naphthalene,
0.10% of dinaphthylsulphones,
14.5% of $H_2SO_4$ and
6.9% of $H_2O$,
are dissolved in 353.4 g of 100% strength sulphuric acid at 10°–15° C. 98.9 g of N-hydroxymethylchloroacetamide (content 99.9%) are uniformly introduced into the solution at 15°–20° C. in the course of 5 hours. The reaction mixture is stirred at 20° C. for 5 hours. It is then diluted with 915 g of water and heated at 105°–110° C. for 3 hours. After only 30 minutes, the 1-aminomethylnaphthalene-6-sulphonic acid starts to precipitate out. The suspension is cooled to 20° C. and the 1-aminonaphthalene-6-sulphonic acid is separated off. It is washed with 100 ml of water and then dried.

Yield 99.5 g (=49% of theory, based on N-hydroxymethylchloroacetamide). Degree of purity of the acid: 93.5%.

The product also contains 1.6% of isomers, 3.1% of sulphuric acid and 1.8% of water.

EXAMPLE 3

(Further processing of 1-aminomethylnaphthalene-6-sulphonic acid to 6-hydroxynaphthalene-1-carboxylic acid)

(α) Oxidation to 1-carboxynaphthalene-6-sulphonic acid (a) 118.6 g (0.5 mol) f 1-aminomethylnaphthalene-6-sulphonic acid (100%) are suspended in 450 ml of 50% strength acetic acid, 140 g (1.0 mol) of hexamethylenetetramine are added and the mixture is heated at the reflux temperature. After 4 hours, 200 ml of concentrated hydrochloric acid are added to the clear solution and the mixture is heated at the reflux temperature for a further hour. Excess formaldehyde is then distilled off, together with acetic acid and water, but the original volume of the reaction mixture is kept constant by addition of water. As soon as no further formaldehyde is detectable in the distillate, the boiling reaction mixture is brought to a pH value of 8 with 50% strength aqueous sodium hydroxide solution, and 110 g (0.7 mol) of potassium permanganate are added. The reaction mixture is heated at the reflux temperature for 1 hour. After the manganese dioxide has been separated off, the reaction solution is brought to a pH value of 3 with concentrated hydrochloric acid. After the reaction mixture has cooled to 20° C., the 1-carboxynaphthalene-6-sulphonic acid obtained in the form of its sodium salt is filtered off.

Yield: 101 g (=80% of theory) of 1-carboxynaphthalene-6-sulphonic acid (100% pure).

(β) 118.6 g (0.5 mol) of 1-aminomethylnaphthalene-6-sulphonic acid (100%) are stirred with 375 ml of water and about 50 g of 45% strength NaOH; the pH value of the mixture is brought to 7–7.5. After addition of 149 g of sodium dichromate (0.5 mol), the mixture is heated at 240° C. in an autoclave for 15 hours. After cooling, the green chromium hydroxide residue is filtered off and washed with hot water. The filtrate is acidified to pH 2 with hydrochloric acid (30% strength) under the influence of heat and then cooled to 20° C. The 1-carboxynaphthalene-6-sulphonic acid which precipitates out in the form of its sodium salt is filtered off and washed with 100 ml of saturated NaCl solution.

Yield: 120 g (=95% of theory) of 1-carboxynaphthalene-6-sulphonic acid (100% pure).

(b) 1-Carboxynaphthalene-6-sulphonic acid is converted into 6-hydroxynaphthalene-1-carboxylic acid by alkali fusion by the procedure described in J. Chem. Soc. 1923, 164 et seq.

What is claimed is:

1. 1-Aminomethylnaphthalene-6-sulphonic acid
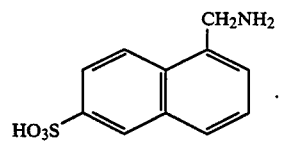
* * * * *